United States Patent
Overes (10) Patent No.: US 7,648,510 B2
(45) Date of Patent: Jan. 19, 2010

(54) ADJUSTMENT APPARATUS

(75) Inventor: Thomas Overes, Winterthur (CH)

(73) Assignee: Zimmer, GmbH, Winterthur (CH)

( * ) Notice: Subject to any disclaimer, the term of this patent is extended or adjusted under 35 U.S.C. 154(b) by 944 days.

(21) Appl. No.: 10/900,814

(22) Filed: Jul. 27, 2004

(65) Prior Publication Data

US 2005/0059980 A1    Mar. 17, 2005

(30) Foreign Application Priority Data

Sep. 15, 2003    (EP) .................... 03020895

(51) Int. Cl.
*A61B 17/58* (2006.01)
*A61F 2/00* (2006.01)

(52) U.S. Cl. ...................................... 606/90

(58) Field of Classification Search ............ 606/86–88, 606/90, 96–98
See application file for complete search history.

(56) References Cited

U.S. PATENT DOCUMENTS

| | | | |
|---|---|---|---|
| 3,532,088 A | 10/1970 | Fiore | |
| 4,349,018 A | 9/1982 | Chambers | |
| 4,364,389 A | 12/1982 | Keller | |
| 4,501,266 A * | 2/1985 | McDaniel | 606/90 |
| 4,524,766 A | 6/1985 | Petersen | |
| 4,566,448 A | 1/1986 | Rohr, Jr. | |
| 4,574,794 A | 3/1986 | Cooke et al. | |
| 4,646,729 A | 3/1987 | Kenna et al. | |
| 4,738,253 A | 4/1988 | Buechel et al. | |
| 4,759,350 A | 7/1988 | Dunn et al. | |
| 4,825,857 A | 5/1989 | Kenna | |
| 4,841,975 A | 6/1989 | Woolson | |
| 4,938,762 A | 7/1990 | Wehrli | |

(Continued)

FOREIGN PATENT DOCUMENTS

DE    20303498 U1    8/2003

(Continued)

*Primary Examiner*—Anu Ramana
(74) *Attorney, Agent, or Firm*—Baker & Daniels LLP (57) ABSTRACT

The invention relates to an adjustment apparatus for the selection of suitable implant sizes in knee operations having a lower work unit supportable at the tibia and an upper work unit supportable at the femur, which are vertically adjustable relative to one another and with which the spacing between the tibia and the femur can be set by spreading apart the knee, wherein the upper work unit includes a carrier vertically adjustable to the lower work unit and at least two different functional units which are releasably conducted to the carrier and of which the one is designed as an extension unit serving for the spreading apart of the knee with the femur in extension and the other is designed as a flexion unit serving for the spreading apart of the knee and for the selection of a suitable implant size with the femur in flexion, wherein the flexion unit includes a base unit couplable to the carrier and a central guide piece which can be suspended at the femur and which can alternatively be brought into a condition freely movable in height or fixed relative to the base section and wherein, when the guide piece is fixed, the knee can be spread by changing the spacing between the lower work unit and the carrier and, when the guide piece is freely movable, the base section is adjustable in height relative to the guide piece which can be suspended at the femur.

18 Claims, 7 Drawing Sheets

U.S. PATENT DOCUMENTS

| Patent No. | | Date | Inventor(s) |
|---|---|---|---|
| 5,002,547 A | | 3/1991 | Poggie et al. |
| 5,067,898 A | * | 11/1991 | Dury .................... 433/75 |
| 5,116,338 A | | 5/1992 | Poggie |
| 5,122,144 A | | 6/1992 | Bert et al. |
| 5,213,112 A | * | 5/1993 | Niwa et al. ............ 600/587 |
| 5,228,459 A | * | 7/1993 | Caspari et al. ......... 128/898 |
| 5,234,433 A | | 8/1993 | Bert |
| 5,250,050 A | | 10/1993 | Poggie et al. |
| 5,306,276 A | | 4/1994 | Johnson et al. |
| 5,326,363 A | | 7/1994 | Aikens |
| 5,342,367 A | | 8/1994 | Ferrante et al. |
| 5,344,423 A | | 9/1994 | Dietz et al. |
| 5,364,401 A | | 11/1994 | Ferrante et al. |
| 5,364,402 A | | 11/1994 | Mumme et al. |
| 5,368,552 A | | 11/1994 | Williamson et al. |
| 5,445,640 A | | 8/1995 | Johnson et al. |
| 5,458,645 A | | 10/1995 | Bertin |
| 5,468,244 A | | 11/1995 | Attfield et al. |
| 5,514,139 A | | 5/1996 | Goldstein et al. |
| 5,527,316 A | | 6/1996 | Stone et al. |
| 5,540,696 A | * | 7/1996 | Booth et al. ............ 606/88 |
| 5,549,686 A | | 8/1996 | Johnson et al. |
| 5,562,675 A | | 10/1996 | McNulty et al. |
| 5,597,379 A | | 1/1997 | Haines et al. |
| 5,601,563 A | | 2/1997 | Burke et al. |
| 5,611,802 A | | 3/1997 | Samuelson et al. |
| 5,628,750 A | | 5/1997 | Whitlock et al. |
| 5,643,272 A | | 7/1997 | Haines et al. |
| 5,669,914 A | | 9/1997 | Eckhoff |
| 5,681,320 A | | 10/1997 | McGuire |
| 5,683,397 A | | 11/1997 | Vendrely et al. |
| 5,688,280 A | | 11/1997 | Booth, Jr. et al. |
| 5,704,941 A | | 1/1998 | Jacober et al. |
| 5,733,292 A | | 3/1998 | Gustilo et al. |
| 5,755,803 A | | 5/1998 | Haines et al. |
| 5,788,700 A | | 8/1998 | Morawa et al. |
| 5,800,438 A | | 9/1998 | Tuke et al. |
| 5,810,827 A | | 9/1998 | Haines et al. |
| 5,824,085 A | | 10/1998 | Sahay et al. |
| 5,860,980 A | | 1/1999 | Axelson et al. |
| 5,879,354 A | | 3/1999 | Haines et al. |
| 5,911,723 A | * | 6/1999 | Ashby et al. ............ 606/88 |
| 5,989,261 A | | 11/1999 | Walker et al. |
| 6,022,377 A | | 2/2000 | Nuelle et al. |
| 6,051,016 A | | 4/2000 | Mesaros et al. |
| 6,056,754 A | | 5/2000 | Haines et al. |
| 6,056,756 A | | 5/2000 | Eng et al. |
| 6,077,270 A | * | 6/2000 | Katz ...................... 606/88 |
| 6,090,114 A | | 7/2000 | Matsuno et al. |
| 6,168,601 B1 | | 1/2001 | Martini |
| 6,197,064 B1 | | 3/2001 | Haines et al. |
| 6,296,646 B1 | | 10/2001 | Williamson |
| 6,475,228 B1 | | 11/2002 | Mesaros et al. |
| 6,478,799 B1 | | 11/2002 | Williamson |
| 6,503,254 B2 | | 1/2003 | Masini |
| 6,575,980 B1 | | 6/2003 | Robie et al. |
| 6,632,225 B2 | | 10/2003 | Sanford et al. |
| 6,648,896 B2 | | 11/2003 | Overes et al. |
| 6,695,848 B2 | | 2/2004 | Haines et al. |
| 6,758,850 B2 | | 7/2004 | Smith et al. |
| 7,094,241 B2 | | 8/2006 | Hodorek et al. |
| 7,201,755 B2 | | 4/2007 | Faoro |
| 7,235,080 B2 | | 6/2007 | Hodorek |
| 7,335,206 B2 | | 2/2008 | Steffensmeier et al. |
| 2002/0198530 A1 | | 12/2002 | Sanford |
| 2003/0100906 A1 | | 5/2003 | Rosa et al. |
| 2003/0225413 A1 | | 12/2003 | Sanford et al. |
| 2003/0233149 A1 | | 12/2003 | Hodorek |
| 2004/0097951 A1 | | 5/2004 | Steffensmeier |
| 2004/0249387 A1 | | 12/2004 | Faoro |
| 2005/0070910 A1 | | 3/2005 | Keene |
| 2006/0030855 A1 | | 2/2006 | Haines |
| 2006/0195111 A1 | | 8/2006 | Couture |
| 2006/0217734 A1 | | 9/2006 | Sanford et al. |
| 2006/0241637 A1 | | 10/2006 | Hodorek et al. |
| 2006/0247647 A1 | | 11/2006 | Hodorek et al. |

FOREIGN PATENT DOCUMENTS

| | | | |
|---|---|---|---|
| DE | 10335410 | * | 2/2005 |
| EP | 0709061 | A1 | 5/1996 |
| EP | 0809969 | B1 | 12/1997 |
| EP | 0839501 | B1 | 5/1998 |
| EP | 0979636 | A2 | 2/2000 |
| EP | 1424042 | B1 | 3/2007 |
| FR | 2648699 | A1 | 12/1990 |
| FR | 2679766 | A1 | 2/1993 |
| FR | 2819168 | A1 | 7/2002 |
| WO | WO01/66021 | A1 | 9/2001 |
| WO | WO01/85038 | A1 | 11/2001 |
| WO | WO 02/17826 | A1 | 3/2002 |

* cited by examiner

ADJUSTMENT APPARATUS

The invention relates to an adjustment apparatus for the selection of suitable implant sizes for knee operations with a lower work unit supportable on the tibia and an upper work unit supportable on the femur, which are vertically adjustable relative to one another and with which the spacing between the tibia and the femur can be adjusted by spreading apart the knee.

Such adjustment apparatuses are generally known, for example from EP 0 979 636 A2. In the known apparatuses, their awkward handling is at times felt to be disadvantageous.

It is the object of the invention to provide an adjustment apparatus of the initially named kind which is as easy to handle as possible and which simultaneously permits a safe and reliable selection of the suitable implant size during the operation.

In one exemplary embodiment, the upper work unit includes a support vertically adjustable relative to the lower work unit and at least two different functional units which are releasably couplable to the support and of which the one is made as an extension unit serving for the spreading apart of the knee when the femur is in extension and the other is made as a flexion unit serving for the spreading apart of the knee as well as for the selection of a suitable implant size when the femur is in flexion, with the flexion unit including a base section couplable to the support and a central guidepiece which can be hung on the femur and which can alternatively be brought into a state freely movable in height or into a fixed state relative to the base section, and with the knee being able to be spread apart, when the guide piece is fixed in place, by changing the spacing between the upper work unit and the support and with the base section being vertically adjustable relative to the guide piece which can be hung on the femur, when the guide piece is freely movable.

An advantage of the adjustment apparatus in accordance with the invention consists of it being able to be used both with a knee in extension and with a knee in flexion due to the different functional units couplable to the support. The surgeon can in particular first spread the knee apart in extension and determine a spacing between the tibia and the femur corresponding to the natural knee in dependence on the ligament tension tangible for him. This spacing value can subsequently be used in flexion as a reference value for the selection of the suitable implant size. For this purpose, only the functional unit has to be replaced, i.e. the flexion unit instead of the extension unit now has to be coupled to the support. The lower work unit of the adjustment apparatus in accordance with the operation can remain in the state supported on the tibia in this process.

A further advantage of the adjustment apparatus in accordance with the invention is the central guide piece which is suspended on the femur in flexion during the operation and is thus fixedly connected to the femur with respect to the spreading apart direction. In accordance with the invention, the central guide piece can alternatively either be fixed in position on the base section or be freely movable relative to the base section, i.e. be released, with respect to the spreading apart direction, i.e. vertically. It is hereby possible for the surgeon to raise the upper work unit as a whole, when the guide piece is fixed in place on the base section, and thus to spread the knee apart. When the central piece is fixed in place, a fixed relative position between the femur and the base section is consequently provided with respect to the spreading apart direction such that, when the guide piece is fixed in place, the desired spacing can be set between the femur and the tibia When the guide piece is, in contrast, freely movable in height relative to the base section, the base section and the femur, on which the guide piece is suspended during the operation, can be moved relatively to one another with respect to the direction of spreading open. Consequently, the surgeon can bring the base section into the desired vertical position relative to the femur, when the guide piece is released.

The invention consequently provides, with one single apparatus, all setting possibilities required for the selection of the suitable implant size, and indeed with particularly simple handling, since the lower work unit can remain supported on the tibia without interruption during the whole operation, i.e. both during the extension phase and during the flexion phase, on the one hand, and it is only necessary to change between the fixed state and the released state of the central guide piece, on the other hand, in order to alternatively bring the femur into the correct vertical position with respect to the tibia or to the base section and thus, for example, to determine the implant size best suitable for the knee to be operated on quickly and simply by iterative trial and error.

Advantageous embodiments of the invention are recited in the dependent claims, in the description and in the drawing.

In accordance with the invention, provision is preferably made for the central guide piece to be rotatable relative to the base section about an axis extending in the spreading apart direction. The femur is hereby free to adopt its natural position relative to the tibia.

It is particularly preferred in this process for the central guide piece to be rotatable relative to the base section both in the freely movable state and in the fixed state. It is hereby ensured that the femur can also adopt its natural position relative to the tibia when it is spread apart with the guide piece fixed to the base section.

The central guide piece can be supported in a guide passage of the base section which is open at at least two oppositely disposed sides and extends in the spreading apart direction, in a displaceable manner in the longitudinal direction of the guide passage and in a rotatable manner about a longitudinal axis of the guide passage.

The central guide piece can furthermore have at least one passage through which a suspension device for the suspension of the guide piece on the femur in flexion can be pushed. The suspension device can in particular be a medullary nail.

The passage can extend obliquely with respect to outer functional regions, in particular locking structures, lying diametrically opposite one another. A matching to the natural oblique extension of the femur with respect to the tibia is hereby advantageously achieved. By turning through 180°, i.e. more or less by "a setting on its head" of the guide piece, it is possible to change between an operation of a left knee and an operation of a right knee.

Provision can furthermore be made for the central guide piece to have at least two passages lying above one another. In this manner, a low construction height of the adjustment apparatus is made possible, since a relatively small guide length, i.e. a relatively small adjustment path in the vertical adjustment of the base section relative to the guide piece can be realized by a targeted selection of the passage for the suspension device, in particular in dependence on the size of the knee.

The central guide piece preferably has a cylindrical basic shape.

The external side of the central guide piece can be provided at least regionally with locking structures with which a locking device of the base section can be brought into and out of engagement for the alternative fixing or releasing of the guide piece. The locking structures can in particular by a toothed arrangement, a corrugated arrangement or a groove/rib arrangement.

The locking device of the base section can include a locking jaw which can be brought into and out of engagement with the central guide piece and which is matched to the locking structures of the guide piece such that a vertical adjustment of the guide piece relative to the base section is prevented in the engaged state, but a rotation of the guide piece is possible.

Furthermore, the locking device of the base section can include a combined rotary/pressure switch actuable with one finger.

Furthermore, provision is made in accordance with the invention for the base section further to include a lower part couplable to the carrier and an upper part which is coupled to the lower part, at which the central guide piece is supported and which is adjustable in the mediolateral direction relative to the lower part together with the central guide piece. The femur cannot hereby only be adjusted relative to the base section with respect to the spreading apart direction, but it is also possible to adjust the base section or its upper part cooperating with the central guide piece perpendicular to the spreading apart direction, and indeed in the mediolateral direction.

The upper part can be made as a carriage which is releasably plugged together with the lower part and which is supported displaceably in the mediolateral direction in the lower part.

Provision can further be made in accordance with the invention for the lower part of the base section to be provided with a display device at which the femur can be aligned in the mediolateral direction by adjusting the upper part. The display device is preferably made such that implant sizes which are suitable and not suitable with respect to the aligned femur can be distinguished from one another by means of the display device. The display device can be provided in the form of two laterally stepped wing sections, with the steps permitting a simple visual size check and every step corresponding to an existing and thus selectable implant size.

The flexion unit preferably furthermore includes a femur probe movable vertically relative to the base section and made for support at the front side of the femur in flexion. On a possible movement of the base section relative to the femur with a released guide piece, the relative position between the femur and the base section corresponding to an existing implant size can be set or checked by means of such a femur probe.

The base section and/or the femur probe can be provided with a display device, in particular in the form of a scale, at which a measure for the implant size dependent on the height of the base section relative to the femur probe can be read off.

Furthermore, provision can be made in accordance with the invention for the carrier and/or the lower work unit to be provided with a display device, in particular in the form of a scale, at which a measure dependent on the height of the carrier relative to the lower work unit for the spacing between the tibia and the femur can be read off.

Provision is furthermore made in accordance with the invention for the base section, in particular its lower part, to be formed as a drill jig and/or as a cutting jig. It is hereby possible, as soon as the base section or its lower part is correctly positioned relative to the femur in flexion, to make bores in the femur via which a cutting block can subsequently be applied to the femur, after the removal of the adjustment apparatus in accordance with the invention, with which the femur can be worked in accordance with the suitable implant size selected by means of the adjustment apparatus in accordance with the invention.

Provision can furthermore be made for the lower work unit for the vertical adjustment of the carrier to have a lever mechanism which, together with a handle of the lower work unit forms a combined holding and actuating device which is made such that a user can hold the adjustment apparatus as a whole by the handle and simultaneously actuate the lever mechanism for the vertical adjustment of the carrier. The handling of the adjustment apparatus in accordance with the invention is hereby further simplified.

The invention will be described in the following by way of example with reference to the drawing. There are shown.

The starting point for the use of the adjustment apparatus in accordance with the invention is a situation in which a respective resection incision has already been carried out at the tibia and at the femur such that, when the knee is in extension, the two resection surfaces lying opposite one another extend parallel to one another. The adjustment apparatus in accordance with the invention serves to find that position at which the posterior femoral incision should be carried out, that is the femoral incision which results in a smooth incision surface which extends parallel to the resection surface of the tibia with the knee in flexion.

The "correct" position for this posterior femoral incision is characterized in that, when the natural ligament tension is taken into account, the spacing between the two resection surfaces in extension is as equal as possible to the spacing between the resection surface of the tibia and the posterior femoral incision surface, on the one hand, and the posterior femoral section is set such that, on the other hand, the thereby resulting anatomical relationships correspond as closely as possible to a pre-determined implant size, since in practice a finite number of implants with a discrete size distribution are available from among which the best suitable implant size has to be selected by means of the adjustment apparatus in accordance with the invention.

Figure 1A:
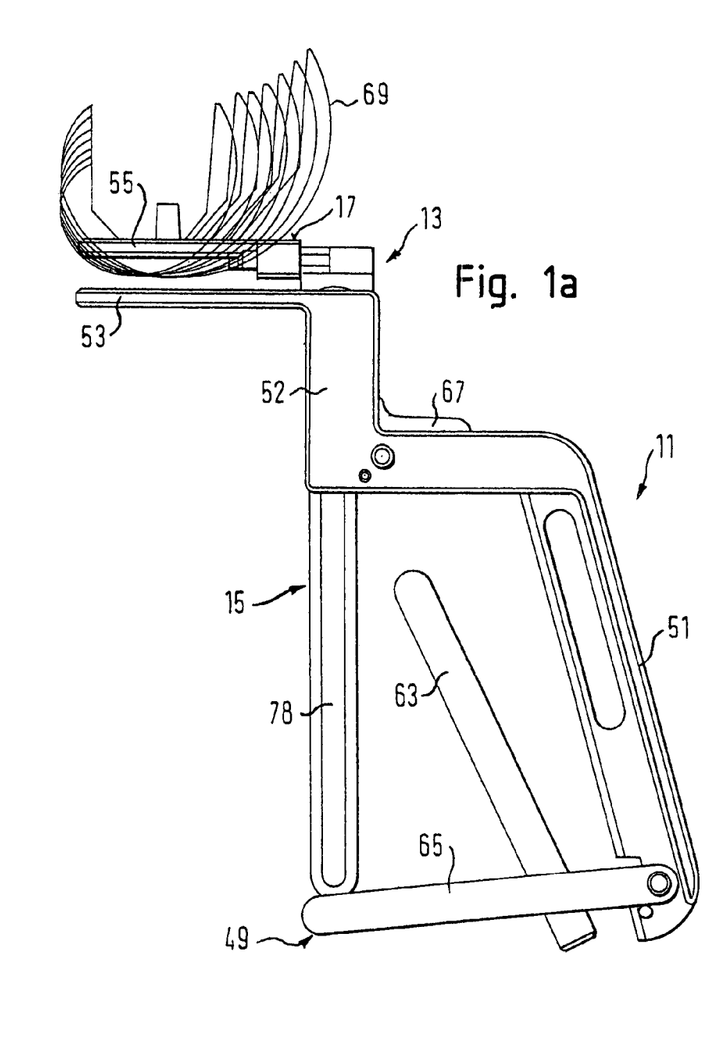
FIGS. 1a, 1b different views of an embodiment of an adjustment apparatus in accordance with the invention in the assembled state in which an extension unit is coupled to the vertically adjustable carrier.
Figure 1B:
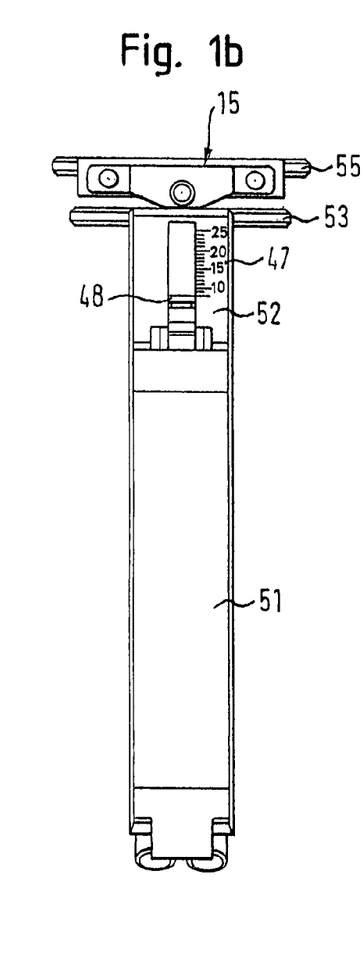

The adjustment apparatus in accordance with the invention includes, in accordance with FIGS. 1a and 1b a lower work unit 11 with a handle 51 and a lever mechanism 49. A lower support plate 53 is formed in one piece at the handle 51 and the lower work unit 11 and thus the total adjustment apparatus can be supported via it on the resection surface of the tibia (not shown).

A carrier 15 described in more detail at another point and including a carrying rod 78 is vertically adjustable relative to the lower work unit 11 via the lever mechanism 49. For this purpose, a first lever 63 is pulled in the direction of the handle 51 by the surgeon, whereby a second lever 65 fixedly connected to the first lever 63 and hinged to the handle 51 moves the carrying rod 78 and thus the carrier 15 upwardly. The carrier 15 can be fixed at a respectively set height by means of a fixing device 67 likewise described in more detail at another point.

The carrier 15 is a component of an upper work unit 13 which includes, in addition to the carrier 15, an extension unit 17 and a flexion unit 19 (FIGS. 2a and 2b) which can alternatively be coupled to the carrier 15 by being plugged onto it.

In FIGS. 1a and 1b, this functional unit of the upper work unit 13 is an extension unit 17 which includes an upper support plate 55 extending parallel to the support plate 53 of the lower work unit 11. The upper support plate 55 contacts the resection surface of the femur in extension with the knee spread apart.

Consequently, by actuating the lever mechanism 49, the knee in extension can be spread apart via the support plates 53, 55 cooperating with the resection surfaces, with this being able to be brought about with one hand by the surgeon since he can hold the whole adjustment apparatus with one hand by the handle 51 and can simultaneously actuate the lever mechanism 49. The surgeon can moreover actuate the fixing device 67 by this hand in order to alternatively release the carrier 15 or fix it at the desired height.

In FIG. 1a, a plurality of femur implants 69 are shown for illustration from among which the implant with the best suitable size should be chosen. The implants 69 are each shown in that position which they would adopt relative to the adjustment apparatus in accordance with the invention when the adjustment apparatus and the implant were simultaneously positioned at the knee in accordance with their intended purpose. FIG. 1a allows it to be recognized that the spacing of the implants 69 from the resection surface of the tibia on which the lower support plate 53 lies is independent of the implant size.

In the extension configuration shown in FIGS. 1a and 1b, the adjustment apparatus in accordance with the invention serves to spread the knee so far apart by enlarging the spacing between the two resection surfaces until the natural position of the femur relative to the tibia has been reached, with the surgeon being able to determine this natural position via the corresponding ligament tension tangible for him. A measure for the "natural" spacing between the two resection surfaces can be read off at a scale 47 (FIG. 1b) which is formed at the transitional section 52 extending in the spreading apart direction between the handle 51 and the lower support plate 53. For this purpose, the carrier 15 is provided with a section which serves as an indicator 48.

Figure 2A:
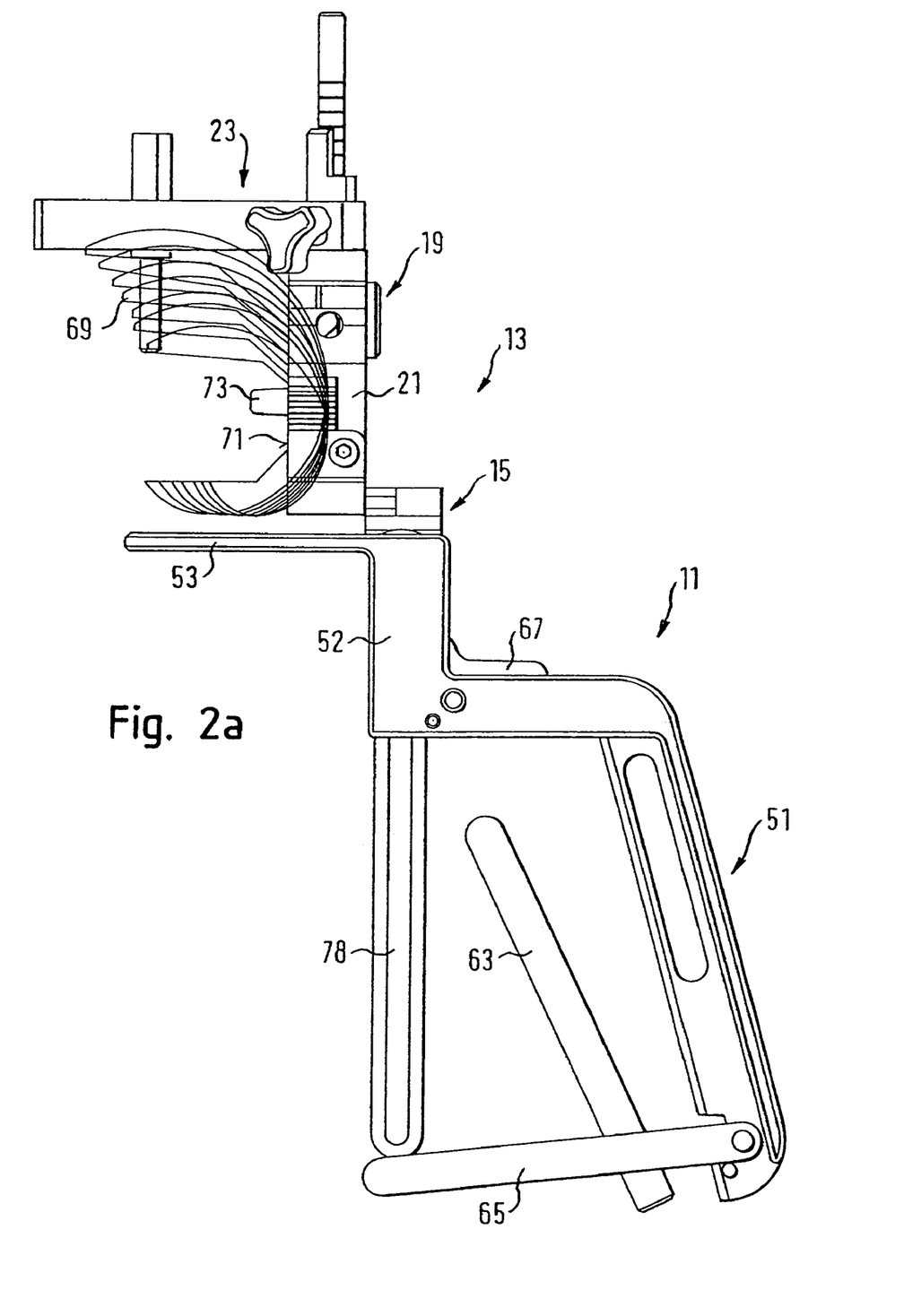
FIGS. 2a, 2b different views of the adjustment apparatus of FIG. 1a with a flexion unit coupled to the carrier.
Figure 2B:
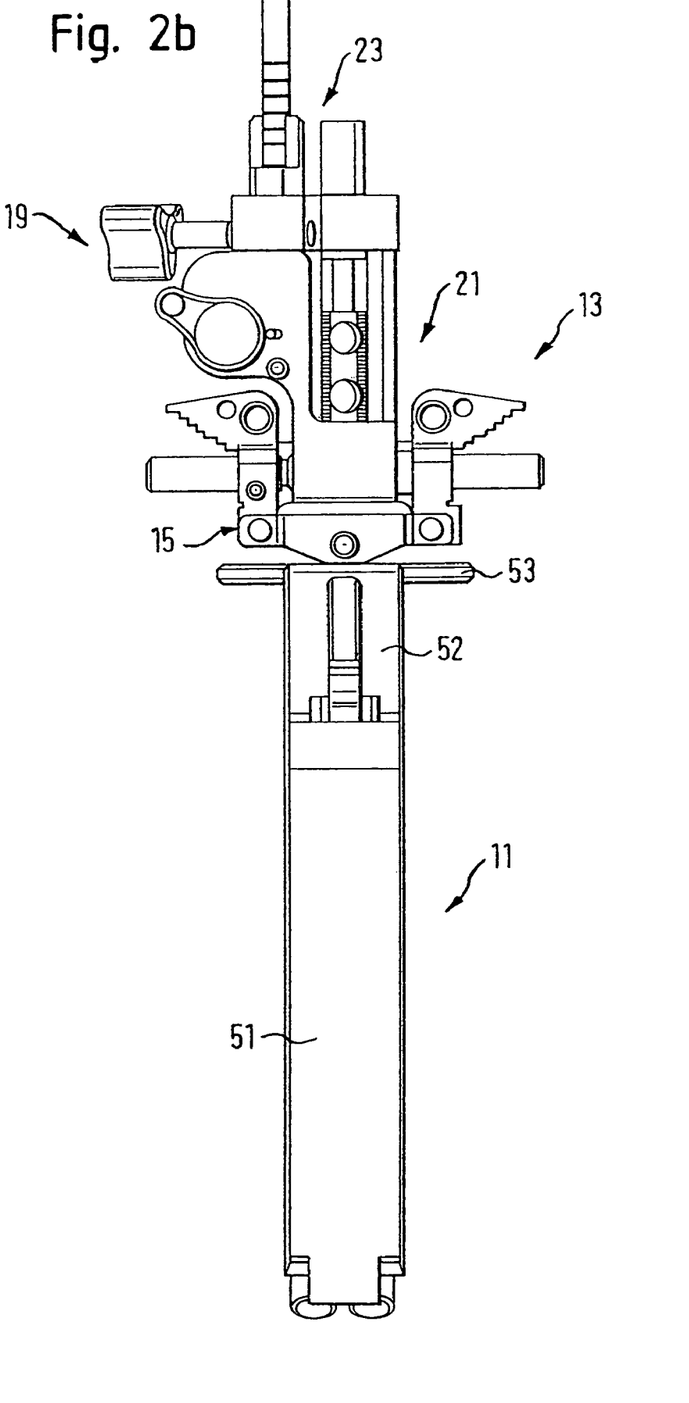

FIGS. 2a and 2b show the adjustment apparatus in accordance with the invention in flexion configuration in which a functional unit serving as the flexion unit 19 is plugged onto the carrier 15. The flexion unit 19 will be described in more detail below in connection with FIGS. 4-8.

FIG. 2a shows in accordance with FIG. 1a the differently sized femur implants 69, but here in an orientation rotated about 90° with respect to FIG. 1a, since the knee is in flexion during the use of the flexion unit 19.

It can be seen from FIG. 2a that the spacing of the femur implants 69 from the resection surface of the tibia is also independent of the implant size in flexion. The position of that inner surface 71 of the implants 69, from which an anchoring pin 71 projects perpendicularly, is likewise independent of the implant size.

The flexion unit 19 of the adjustment apparatus in accordance with the invention provides all adjustment possibilities which are required to select, by varying the height and the mediolateral position of a component of the flexion unit 19 serving as a drill jig and described in more detail later relative to the femur, from the set of available femur implants 69 the best suitable implant size, with the "best suitable" implant size being that which permits a motion which comes as close as possible to the natural motion of the knee.

Figure 3A:
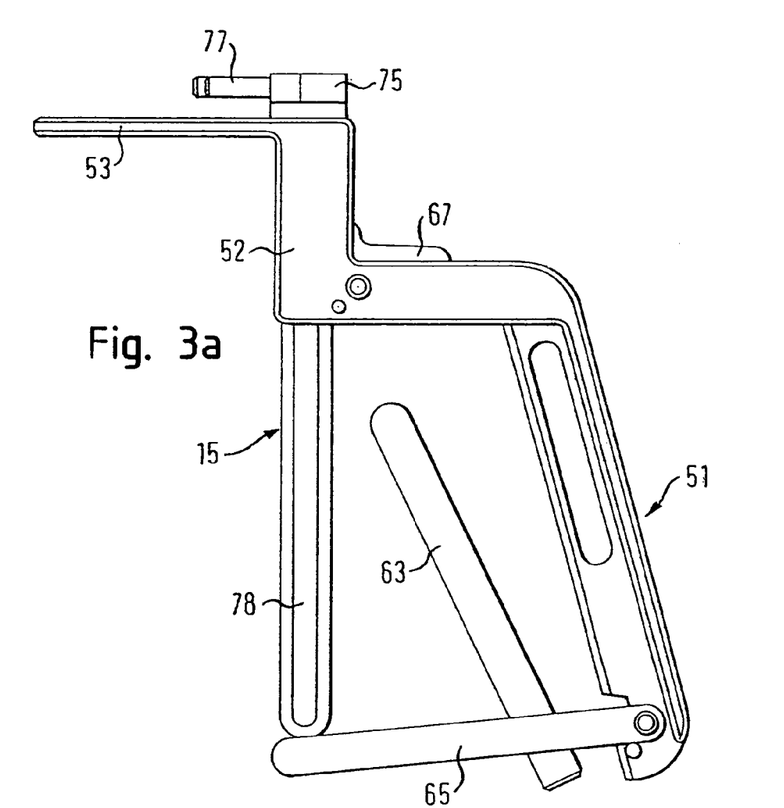
FIGS. 3a-3c the lower work unit and the carrier of the adjustment apparatus of FIGS. 1a and 1b.
Figure 3B:
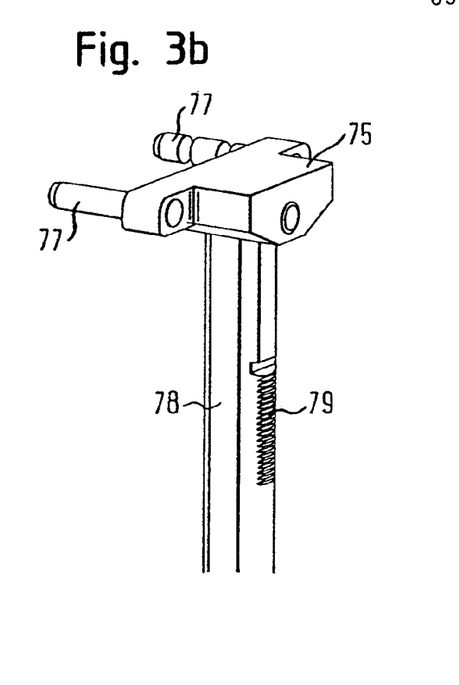
Figure 3C:
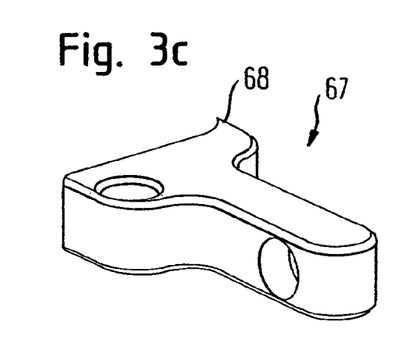

FIG. 3a shows the carrier 15 coupled to the lower work unit 11 without the functional unit pushed on. As FIG. 3b shows, the carrier 15 includes a head part 75 with two carrying pins 77 which form a push-on fork and onto which the functional units—i.e. the extension unit 17 in accordance with FIGS. 1a and 1b and the flexion unit 19 in accordance with FIGS. 2a and 2b—can alternatively be pushed on and the carrying rod 78. The carrying rod 78 is regionally provided with a toothed arrangement or a corrugation 79, into which a locking tooth 68 of the fixing device 67 shown in FIG. 3c and rotatably attached to the lower work unit 11 can engage in a latching manner in order to fix the carrying rod 78, and thus the carrier 15 together with the functional unit held by it in each case, at the desired height relative to the lower work unit 11.

Figures 4A, 4B:
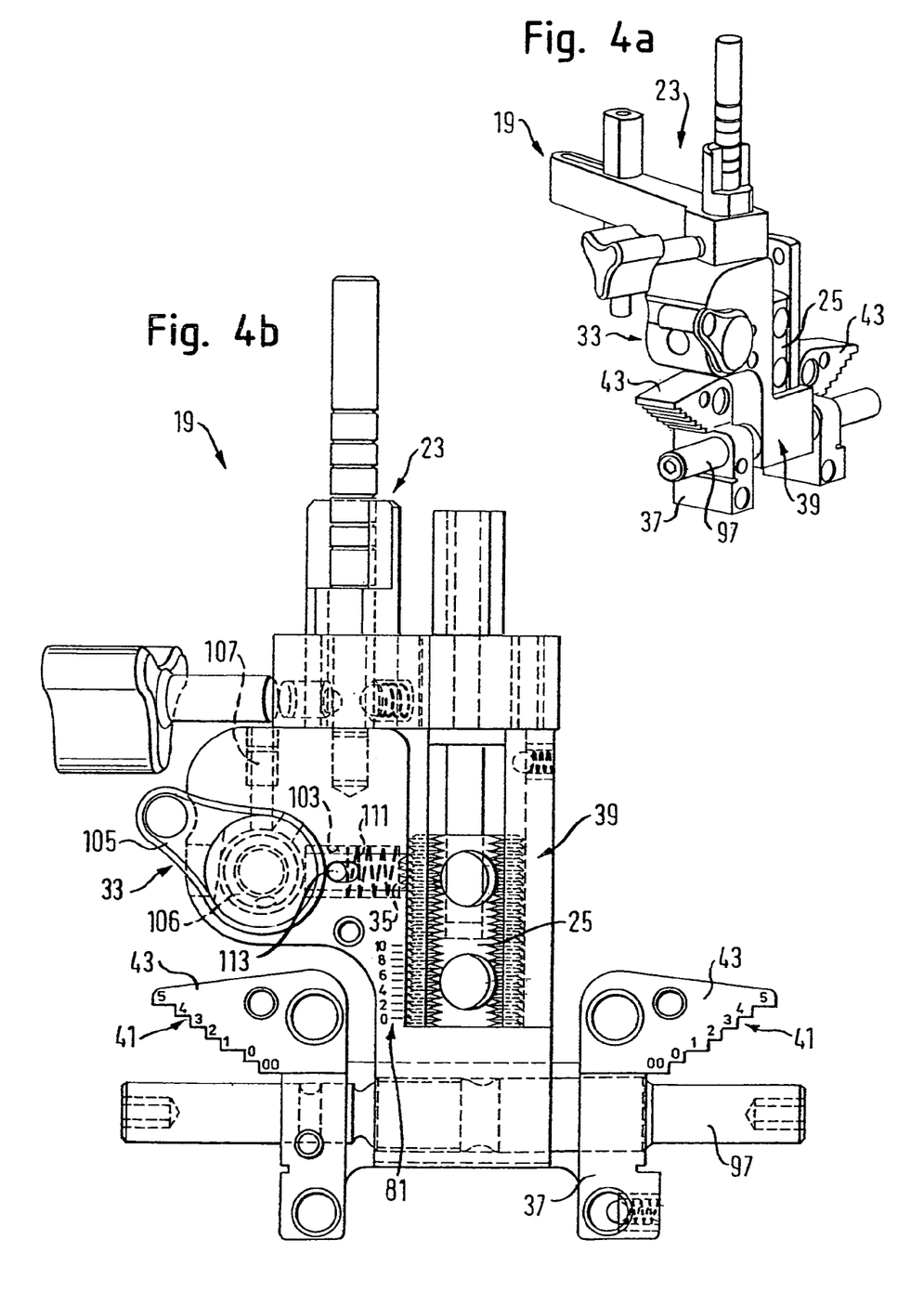
FIGS. 4a, 4b different views of the flexion unit of the adjustment apparatus in the configuration of FIGS. 2a, 2b.

In accordance with FIGS. 4a and 4b, the flexion unit 19 includes a symmetrically formed lower part 37, an upper part 39 which is displaceably supported at the lower part 37 transversely—i.e. in the mediolateral direction—relative to the lower part 37 and which forms a base section 21 (FIGS. 2a, 2b) of the flexion unit 19 together with the lower part 37, a femur probe 23 attached vertically adjustably to the upper part 39, a central guide piece 25 and a locking device 33 integrated into the upper part 39 for the alternative fixing and releasing of the central guide piece 25 relative to the upper part 39.

Reference will also be made to FIGS. 5-8 in the following for the more detailed explanation of the flexion unit 19.

The lower part 37, which is provided with carrier passages 83 for the pushing onto the pins 77 of the carrier 15 (cf. FIGS. 3a, 3b), is provided with two lateral stepped wing sections 43, whose steps form a display device 41 which serves to align the femur in the mediolateral direction and to check an implant size considered for selection actually during the operation as to whether this implant size can be used with respect to the mediolateral dimensions of the femur or of the resection surface formed at the femur, i.e. whether the implant has a suitable width.

A correct position of the femur relative to the lower part 37 in the mediolateral direction is also important because the lower part 37—which, together with the upper part 39, areally contacts the resection surface of the femur in flexion during the operation—is made as a drill jig and is provide with passages 85, 87 for this purpose. The large passages 85 serve as drill guides for pins, also known as "pegs", which simultaneously serve as drills and as positioning pins and on which a cutting block runs (not shown) subsequently to the adjusting procedure. The purpose of the adjustment apparatus in accordance with the invention ultimately consists of finding the optimum position for these pegs and thus for the cutting block. The small, obliquely extending passages 87 can be used to receive so-called "cross-pins" with which the adjustment apparatus is fixed to the knee.

A flat parallelepiped shaped web 89 onto which the upper part (FIGS. 5a, 6) can be pushed from above and along which the upper part 39 is displaceable transversely—i.e. in the mediolateral direction—to the lower part 38, extends between the two wing sections 43 of the lower part 37 shaped like a whistle. For this purpose, the upper part 39 is provided with a slot cut-out 91 matching the web 89.

The upper part 39 furthermore has a transverse passage 93 extending parallel to the slot cut-out 91 and with a circular cross-section which is aligned in the assembled state in accordance with FIGS. 4a, 4b with corresponding transverse passages 95 of the lower part 37. The upper part 39 and the lower part 37 are fixedly held together via the passages 93, 95 by means of a spindle 97 in the spreading apart direction such that a vertical adjustment of the lower part 37 and the upper part 39 is only possible together. By actuating the spindle 97, the upper part 39 and the lower part 37 are displaced relative to one another in the longitudinal direction of the spindle 97, that is perpendicular to the spreading apart direction, in order to carry out the aforesaid matching or measurement in the mediolateral direction by means of the stepped wing sections 43.

Furthermore, a guide passage 27 is formed in the upper part 39 in the spreading apart direction which is open at two mutually opposite sides and into which the central guide piece 25 having a cylindrical basic shape can be inserted from above. The guide passage 27 and the guide piece 25 are matched to one another such that the guide piece 25 is displaceable in the spreading apart direction relative to the upper part 39 inside the guide passage 27 without any substantial lateral clearance and is rotatable about an axis extending parallel to the spreading apart direction and coinciding with the longitudinal axis of the guide passage 27 and of the guide piece 25.

Two outer regions of the guide piece 25 lying opposite one another are each provided with a toothed arrangement or corrugation 31 which are formed by a groove and rib arrangement and which form locking structures of the guide piece 25 into which the fixing device 33 of the upper part 39 described in more detail below can latchingly engage in order to fix the guide piece 25 in a desired height with respect to the upper part 39.

Figures 5A, 5B, 5C, 5D, 6, 7A, 7B, 7C, 8:
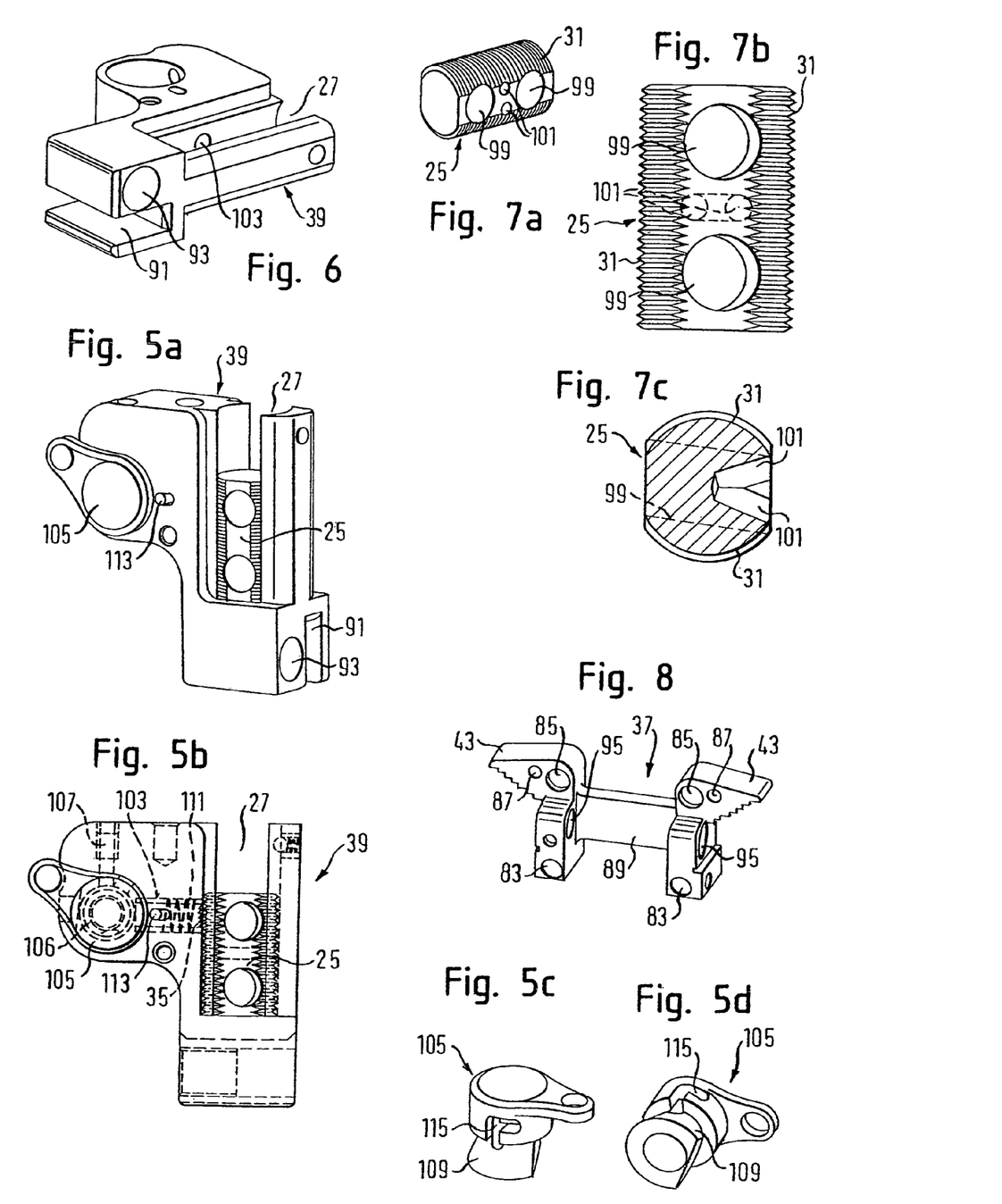
FIGS. 5a-5d different views of the upper part and of the central guide piece of the flexion unit of FIGS. 4a, 4b in the assembled state and of a rotary/pressure switch integrated in the upper part.
FIG. 6 the upper part of FIGS. 5a, 5b without a guiding piece and without a rotary/pressure switch.
FIGS. 7a-7c different views of the central guide piece of FIGS. 5a, 5b.
FIG. 8 the lower part of the flexion unit of FIGS. 4a, 4b.

As in particular FIGS. 7b and 7c show (FIG. 7c is a section through the guide piece 25 along the central plane extending perpendicular to the longitudinal axis of the guide piece 25), the guide piece 25 is provided with two suspension passages 99 spaced apart in the axial direction and each extending not symmetrically, but obliquely through the guide piece 25 with respect to the outside regions forming the locking structures 33. Furthermore, the guide piece 25 is provided between the two suspension passages 99 at the height of the central plane perpendicular to the longitudinal axis with two blind bores 101 which extend in a V shape and which open at an outer side of the guide piece 25 between the structured regions 31 and end and merge into one another before reaching the central plane of the guide piece 25 extending in the longitudinal direction. Boundary pins (not shown) can be inserted, e.g. pressed, into these blind bores and serve as rotary abutments for the guide piece 25 and bound the rotatability of the guide piece 25 in the guide passage 27 such that the full cross-section of the passages 99 is always available for the introduction of the medullary nail.

During the operation, a medullary nail (not shown) is guided through one of the suspension passages of the guide piece 25 and is inserted into the femur via the resection surface of the femur, which is contacted by the upper part 39 and the lower part 37, in order to suspend the guide piece 25 located in the guide passage 27 and thus the flexion unit 19 at the femur. To permit the guiding through of the medullary nail, the guide passage 27 is open at the two longitudinal sides lying opposite one another.

The fixing device 33 of the upper part 39 includes a locking jaw 35 which is formed as a sliding pin, cooperates with a spring 111 and is displaceably arranged in a transverse passage 103 extending perpendicular to the guide passage 27 and opening into the guide passage 27. At its end face cooperating with the guide piece 25, the locking jaw 35 is provided with a corrugation or toothed arrangement likewise formed by a groove and rib arrangement which is matched to the locking structures 31 of the guide piece 25 such that the structures can engage into one another such that the guide piece 25 is admittedly hindered from making a movement relative to the upper part 39 in the spreading apart direction, but a rotation of the guide piece 25 relative to the upper part 39 is possible.

The fixing device 33 furthermore includes a combined rotary/pressure switch 105 which cooperates with the locking jaw 35 displaceable in the transverse passage 103, on the one hand, and with a latching pin 107, on the other hand. FIGS. 5a and 5b (cf. also FIG. 4b) show the released condition of the fixing device 33 in which the locking jaw 35 is out of engagement with the guide piece 25. The switch 105 is in the pressed-in state in which it is held by the latching pin 107 as long as it is not rotated counter-clockwise in FIG. 4b and FIGS. 5a, 5b.

When the switch 105 is rotated out of the released position, the latching pin 107 releases the switch 105 such that it is outwardly pressed out of the upper part 39 by a spring 106 compressed in the released condition, whereby the end of the locking jaw 35 facing the switch 105 is pressed into engagement with the guide piece 25 by a conical control surface 109 of the switch 105 (FIGS. 5c and 5d). This engagement movement takes place against the restoring force of a spring 111 which surrounds the locking jaw 35 and is tensioned by a perpendicularly projecting pin 113 of the locking jaw 35, i.e. the spring 106 pressing the switch 105 out can overcome the restoring force of the spring 111.

The region of the switch 105 having the shape of a truncated cone and provided with the conical control surface 109 is not rotationally symmetrical in design, but cut away at a side.

FIGS. 5c and 5d moreover show that the switch 105 has an L-shaped control groove 115 into which the latching pin 107 engages. The switch 105 is held via the section of the control groove 115 extending in the peripheral direction by the latching pin 107 in the pressed-in position corresponding to the released condition in accordance with FIGS. 4b and 5a, 5b, whereas the section of the control groove 115 extending in the radial direction permits the switch 105 to be able to jump out due to the relaxing spring 106 after a corresponding rotation and to be able to push the latching jaw 35 into engagement with the guide piece 25 via the conical control surface 109.

As in particular FIG. 5a shows, the pin 113 of the locking jaw 35 is guided in an elongate bore of the upper part 39, whereby the correct orientation between the toothed arrangements of the locking jaw 35 and of the guide piece 25 is ensured.

Figures 9, 10:
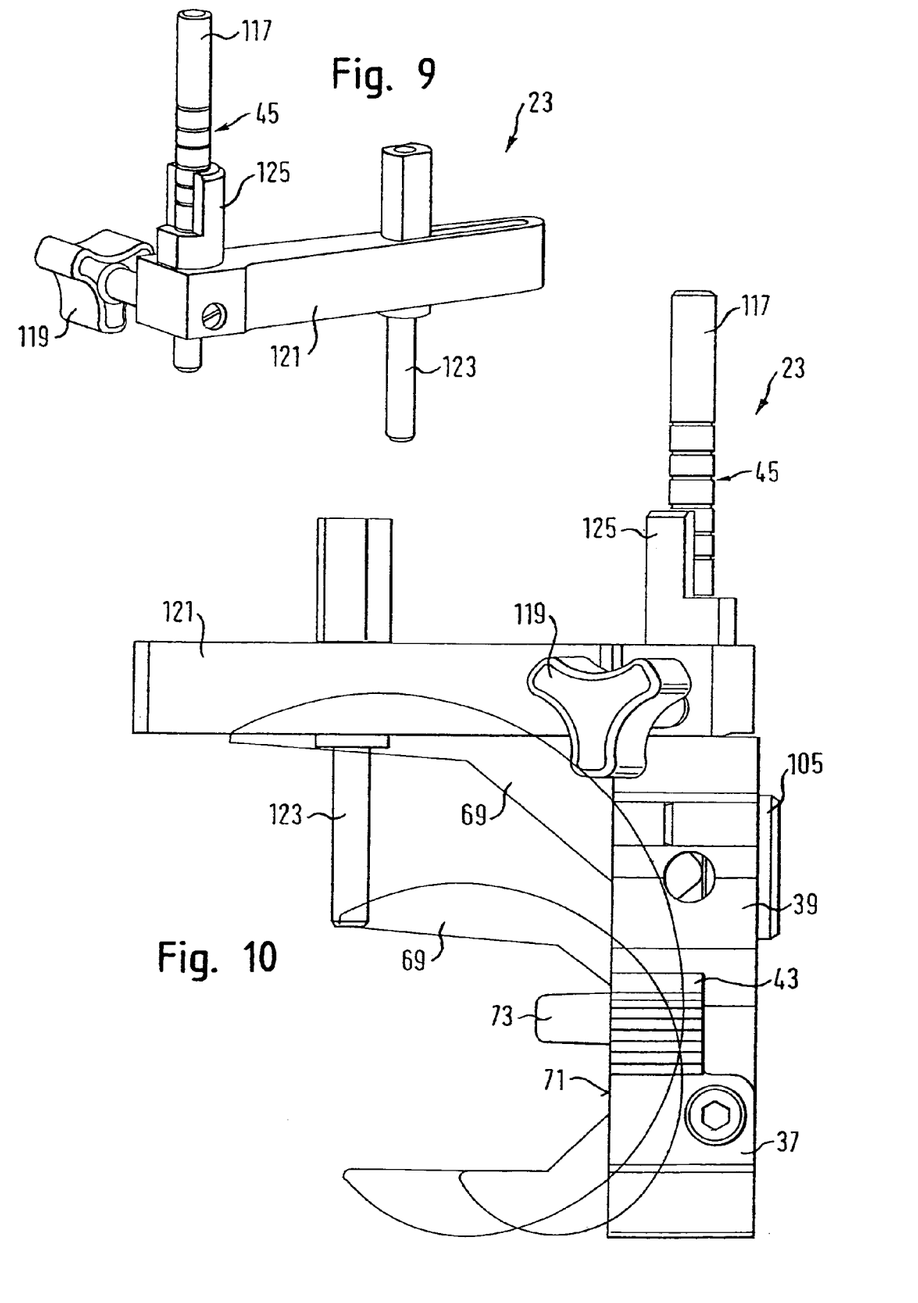
FIG. 9 the femur probe of the flexion unit of FIGS. 4a, 4b.
FIG. 10 a side view of FIG. 4 for the explanation of the functional manner of the femur probe.

The femur probe 23 in accordance with FIGS. 9 and 10 includes a pin 117 which is provided with a scale 45, can be pushed onto the upper part 39 and can be fixed there by means of a clamping screw 119. A probe pin 123 is attached to a probe arm 121 extending perpendicular to the pin 117 and rotatable with respect to the pin 117 and extends parallel to the pin 117 and thus in the spreading apart direction and is displaceable in an elongate bore of the probe arm 121 along the probe arm 121. Movements of the probe pin 123 relative to the probe arm in the spreading apart direction are not possible.

The lower free end of the probe pin 121 in FIGS. 9 and 10 rests on the anterior side of the femur in flexion during the use of the flexion unit 19. Relative movements between the upper part 39 and the femur in the direction of spreading part, which are possible when the guide piece 25 is released, result in a displacement of the probe arm 121 relative to the upper part 39 and thus relative to the pin 117 pushed onto the upper part 39 and to the scale 45 attached to this. An attachment 125 of the probe arm 121 serves as an indicator in this process via which the respective scale value can be read off.

The scale 45 is selected such that each scale mark corresponds to an available implant size. Consequently, when the guide piece 25 is released, the height of the upper part 39 and thus of the lower part 37 formed as a drill jig relative to the femur can be set such that this height precisely corresponds to an existing implant size, and indeed with respect to the size of the implant in the direction anterior-posterior. This implant size can be checked as to its suitability as the best suitable implant size with the help of the stepped wing sections 43 of the lower part 37, at which each step corresponds to an existing implant size, as well as with the help of the scale 47 formed on the carrier 15 (FIG. 1*b*). The scale 47 is used both in extension and in flexion.

To be able to set reproducible configurations on a change of the relative position between the upper part 39 and the guide piece 25, the upper part 39 is provided with a display device 81 (FIG. 4*b*) in the form of a scale on which, e.g. via the lower edge of the guide piece 25, a measure for its height relative to the upper part 39 can be read off. Consequently, a measure is available to the surgeon for a correction adjustment which may become necessary if it is found, for example, with the knee in flexion that an implant size initially taken into consideration would result in ligaments which would be too loose, whereupon the initially considered incision height is changed in that a corresponding vertical adjustment of the upper part 39 relative to the guide piece 25 is carried out. A measure for this change of the incision height can then be read off at the scale 81.

The adjustment apparatus in accordance with the invention permits the selection of a best suitable implant size by locating the optimum position of the lower part 37 formed as the drill jig relative to the femur while taking the correct spacing into account between the resection surfaces of the tibia and of the femur, taking the mediolateral alignment of the lower part 37 to the femur into account and taking the existing implant sizes into account from which the best suited implant for the respective operation should be selected.

REFERENCE SYMBOL LIST 11 lower work unit
13 upper work unit
15 carrier
17 extension unit
19 flexion unit
21 base section
23 femur probe
25 central guide piece
27 guide passage of the base section
31 locking structures of the guide piece
33 locking device of the base section
35 locking jaw
37 lower part
39 upper part
41 display device of the lower part
43 stepped wing section of the lower part
45 display device of the lower part
47 display device of the lower work unit
48 indicator of the carrier
49 lever mechanism
51 handle
52 transition section
53 lower support plate
55 upper support plate
63 first lever
65 second lever
67 fixing device
68 locking tooth
69 femur implant
71 interior surface of the implant
73 anchoring pin of the implant
75 head part
77 carrying pin
78 carrying rod
79 toothed arrangement
81 display device of the base section
83 carrier passage of the lower part
85 passage of the lower part
87 passage of the lower part
89 transverse web
91 slot cut-out
93 transverse passage of the upper part
95 transverse passage of the lower part
97 spindle
99 suspension passage of the guide piece
101 blind bore
103 transverse passage
105 rotary/pressure switch
106 spring of the rotary/pressure switch
107 latching pin
109 conical control surface
111 spring of the locking jaw
113 pin of the locking jaw
115 L-shaped control groove
117 pin of the femur probe
119 clamping screw
121 probe arm
123 probe pin
125 attachment

The invention claimed is:

1. An adjustment apparatus for the selection of suitable implant sizes in knee operations comprising a lower work unit supportable on a tibia and an upper work unit supportable on a femur, wherein the lower work unit and the upper work unit are vertically adjustable relative to one another and with which the spacing between the tibia and the femur can be adjusted by spreading apart the knee, wherein the upper work unit includes a carrier that is vertically adjustable relative to the lower work unit and at least two different functional units which are releasably couplable to the carrier, wherein one of the at least two different functional units is formed as an extension unit serving for the spreading apart of the knee when the femur is in extension, and another of the at least two different functional units is formed as a flexion unit serving for the spreading apart of the knee and for the selection of a suitable implant size when the femur is in flexion, wherein the flexion unit includes a base section couplable to the carrier and a central guide piece which can alternatively be brought into a condition freely movable in height or fixed relative to the base section, wherein the central guide piece is rotatable relative to the base section about an axis extending in the spreading apart direction and wherein, when the central guide piece is fixed, the knee can be spread apart by changing the spacing between the lower work unit and the carrier and, when the central guide piece is freely movable, the base section is adjustable in height relative to the central guide piece.

2. The adjustment apparatus of claim 1, wherein the central guide piece is rotatable relative to the base section both in the freely movable state and in the fixed state.

3. The adjustment apparatus of claim 1, wherein the central guide piece is supported in a guide passage of the base section open at at least two mutually opposite sides and extending in the direction of spreading apart, in a displaceable manner in the longitudinal direction of the guide passage.

4. The adjustment apparatus of claim 1, wherein the central guide piece has at least one passage through which a suspension device can be inserted.

5. The adjustment apparatus of claim 4, wherein the passage extends obliquely with respect to outer functional regions lying diametrically opposite one another.

6. The adjustment apparatus of claim 4, wherein the central guide piece has at least two passages lying above one another.

7. The adjustment apparatus of claim 1, wherein the central guide piece has a cylindrical base shape.

8. The adjustment apparatus of claim 1, wherein the external side of the central guide piece is provided at least regionally with locking structures, wherein the lock structure is one of a toothed arrangement, a corrugation, and a groove and rib arrangement, with which a locking device of the base section can be brought into and out of engagement for the alternative fixing and releasing of the central guide piece.

9. The adjustment apparatus of claim 8, wherein the locking device of the base section includes a locking jaw which can be brought into and out of engagement with the central guide piece and which is matched to the locking structures of the central guide piece such that a vertical adjustment of the central guide piece relative to the base section is prevented in the engaged state, but a rotation of the central guide piece is possible.

10. The adjustment apparatus of claim 8, wherein the locking device of the base section includes a combined rotary/pressure switch actuable with one finger.

11. The adjustment apparatus of claim 1, wherein the flexion unit furthermore includes a femur probe movable vertically relative to the base section and made for support at the anterior side of the femur in flexion.

12. The adjustment apparatus of claim 11, wherein at least one of the base section and the femur probe is provided with a display device at which a measure for the implant size dependent on the height of the base section relative to the femur probe can be read.

13. The adjustment apparatus of claim 1, wherein at least one of the carrier and the lower work unit is provided with a display device at which a measure dependent on the height of the carrier relative to the lower work unit for the spacing between the tibia and the femur can be read.

14. The adjustment apparatus of claim 1, wherein the base section is formed as at least one of a drill jig and a cutting jig.

15. An adjustment apparatus for the selection of suitable implant sizes in knee operations comprising a lower work unit supportable on a tibia and an upper work unit supportable on a femur, wherein the lower work unit and the upper work unit are vertically adjustable relative to one another and with which the spacing between the tibia and the femur can be adjusted by spreading apart the knee, wherein the upper work unit includes a carrier that is vertically adjustable relative to the lower work unit and at least two different functional units which are releasably couplable to the carrier, wherein one of the at least two different functional units is formed as an extension unit serving for the spreading apart of the knee when the femur is in extension, and another of the at least two different functional units is formed as a flexion unit serving for the spreading apart of the knee and for the selection of a suitable implant size when the femur is in flexion, wherein the flexion unit includes a base section couplable to the carrier and a central guide piece which can alternatively be brought into a condition freely movable in height or fixed relative to the base section, wherein, when the central guide piece is fixed, the knee can be spread apart by changing the spacing between the lower work unit and the carrier and, when the central guide piece is freely movable, the base section is adjustable in height relative to the central guide piece, wherein the base section further includes a lower part couplable to the carrier and an upper part which is coupled to the lower part, at which the central guide piece is supported and which is adjustable in the mediolateral direction relative to the lower part together with the central guide piece.

16. The adjustment apparatus of claim 15, wherein the upper part is formed as a slide releasably plugged together with the lower part and displaceably supported at the lower part in the mediolateral direction.

17. The adjustment apparatus of claim 15, wherein the lower part of the base section is provided with a display device, at which the femur can be aligned in the mediolateral direction by adjusting the upper part, with implant sizes suitable and not suitable with respect to the aligned femur being able to be distinguished by means of the display device.

18. An adjustment apparatus for the selection of suitable implant sizes in knee operations comprising a lower work unit supportable on a tibia and an upper work unit supportable on a femur, wherein the lower work unit and the upper work unit are vertically adjustable relative to one another and with which the spacing between the tibia and the femur can be adjusted by spreading apart the knee, wherein the upper work unit includes a carrier that is vertically adjustable relative to the lower work unit and at least two different functional units which are releasably couplable to the carrier, wherein one of the at least two different functional units is formed as an extension unit serving for the spreading apart of the knee when the femur is in extension, and another of the at least two different functional units is formed as a flexion unit serving for the spreading apart of the knee and for the selection of a suitable implant size when the femur is in flexion, wherein the flexion unit includes a base section couplable to the carrier and a central guide piece which can alternatively be brought into a condition freely movable in height or fixed relative to the base section, wherein, when the central guide piece is fixed, the knee can be spread apart by changing the spacing between the lower work unit and the carrier and, when the central guide piece is freely movable, the base section is adjustable in height relative to the central guide piece, wherein, for the vertical adjustment of the carrier, the lower work unit has a lever mechanism which, together with a handle of the lower work unit, forms a combined holding and actuating device, wherein a user can hold the adjustment apparatus as a whole by the handle and can simultaneously actuate the lever mechanism for the vertical adjustment of the carrier.

* * * * *

UNITED STATES PATENT AND TRADEMARK OFFICE
CERTIFICATE OF CORRECTION

PATENT NO.      : 7,648,510 B2                              Page 1 of 1
APPLICATION NO. : 10/900814
DATED           : January 19, 2010
INVENTOR(S)     : Thomas Overes It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1514 days.

Signed and Sealed this

Twenty-third Day of November, 2010

David J. Kappos
*Director of the United States Patent and Trademark Office*